US008532781B1

(12) United States Patent
Vanpoucke

(10) Patent No.: US 8,532,781 B1
(45) Date of Patent: Sep. 10, 2013

(54) METHODS AND SYSTEMS OF GENERATING A GRAPHICAL REPRESENTATION OF AN INTRACOCHLEAR TRAJECTORY OF ELECTRODES

(75) Inventor: Filiep J. Vanpoucke, Huldenberg (BE)

(73) Assignee: Advanced Bionics, LLC, Valencia, CA (US)

( * ) Notice: Subject to any disclaimer, the term of this patent is extended or adjusted under 35 U.S.C. 154(b) by 349 days.

(21) Appl. No.: 12/560,626

(22) Filed: Sep. 16, 2009

Related U.S. Application Data

(60) Provisional application No. 61/097,983, filed on Sep. 18, 2008.

(51) Int. Cl.
*A61N 1/00* (2006.01)
(52) U.S. Cl.
USPC .................................................. 607/57
(58) Field of Classification Search
USPC ........................ 607/55–57; 128/898–899
See application file for complete search history.

(56) References Cited

U.S. PATENT DOCUMENTS

| | | | | |
|---|---|---|---|---|
| 5,626,629 | A * | 5/1997 | Faltys et al. | 607/57 |
| 7,103,417 | B1 * | 9/2006 | Segel et al. | 607/57 |
| 7,107,101 | B1 * | 9/2006 | Faltys | 607/55 |
| 8,027,733 | B1 * | 9/2011 | Fridman et al. | 607/57 |
| 2006/0247735 | A1 * | 11/2006 | Honert | 607/57 |
| 2007/0156202 | A1 * | 7/2007 | Zierhofer | 607/57 |
| 2007/0179565 | A1 * | 8/2007 | Overstreet et al. | 607/57 |
| 2008/0194922 | A1 * | 8/2008 | Holden | 600/300 |
| 2009/0132005 | A1 * | 5/2009 | van den Honert et al. | 607/57 |
| 2009/0132006 | A1 * | 5/2009 | van den Honert et al. | 607/57 |

\* cited by examiner

*Primary Examiner* — Christopher D Koharski
*Assistant Examiner* — Catherine Voorhees
(74) *Attorney, Agent, or Firm* — ALG Intellectual Property, LLC

(57) ABSTRACT

Exemplary methods and systems of generating a graphical representation of an intracochlear trajectory of electrodes include using electrical field imaging to generate an electrical field spread curve for each of a plurality of electrodes contained within an electrode array at least partially inserted within a cochlear implant patient and generating a graphical representation of an intracochlear trajectory of the electrodes based on the electrical field spread curves.

20 Claims, 16 Drawing Sheets

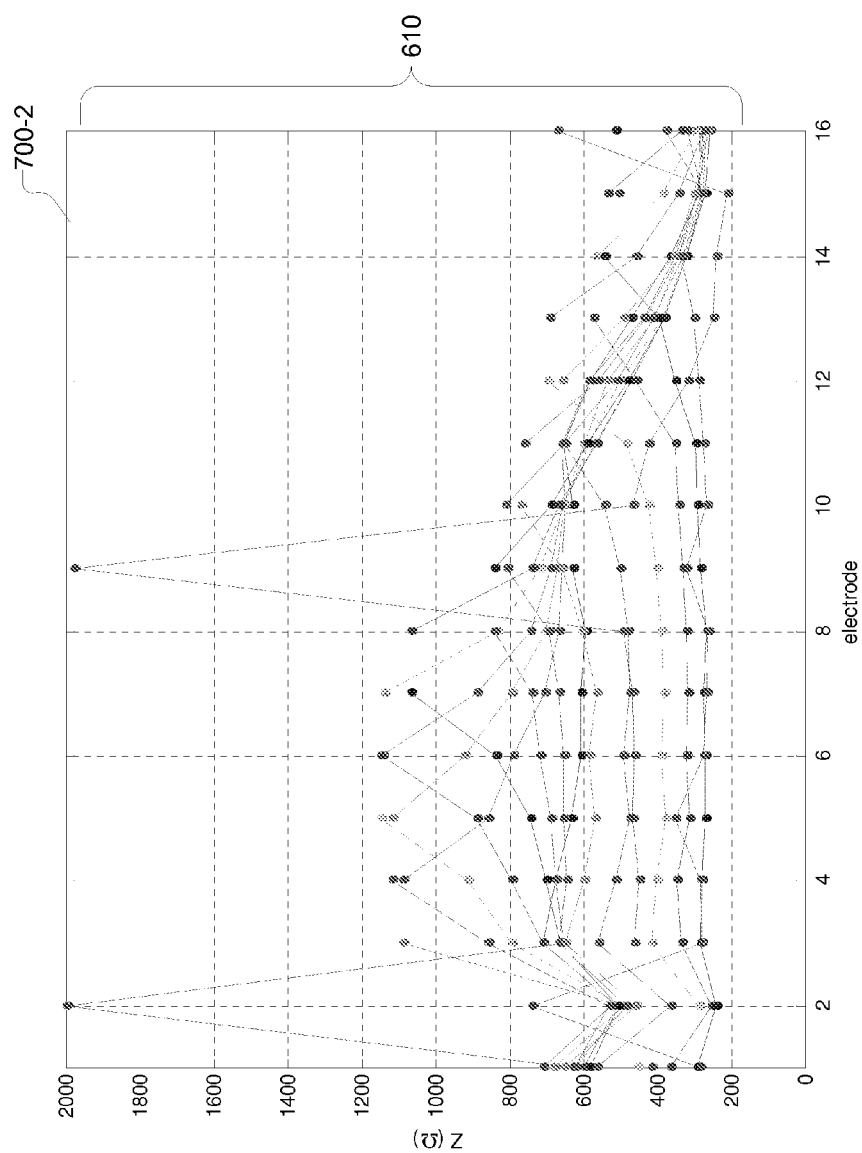

METHODS AND SYSTEMS OF GENERATING A GRAPHICAL REPRESENTATION OF AN INTRACOCHLEAR TRAJECTORY OF ELECTRODES

RELATED APPLICATIONS

The present application claims priority under 35 U.S.C. §119(e) to U.S. Provisional Patent Application No. 61/097,983 by Filiep J. Vanpoucke, filed on Sep. 18, 2008, and entitled "Methods and Systems of Generating a Graphical Representation of an Intracochlear Trajectory of Electrodes," the contents of which are hereby incorporated by reference in their entirety.

BACKGROUND

The sense of hearing in human beings involves the use of hair cells in the cochlea that convert or transduce audio signals into auditory nerve impulses. Hearing loss, which may be due to many different causes, is generally of two types: conductive and sensorineural. Conductive hearing loss occurs when the normal mechanical pathways for sound to reach the hair cells in the cochlea are impeded. These sound pathways may be impeded, for example, by damage to the auditory ossicles. Conductive hearing loss may often be helped by the use of conventional hearing aids that amplify sound so that audio signals reach the cochlea and the hair cells. Some types of conductive hearing loss may also be treated by surgical procedures.

Sensorineural hearing loss, on the other hand, is due to the absence or the destruction of the hair cells in the cochlea which are needed to transduce audio signals into auditory nerve impulses. Thus, many people who suffer from severe to profound sensorineural hearing loss are unable to derive any benefit from conventional hearing aid systems.

To overcome sensorineural hearing loss, numerous cochlear implant systems—or cochlear prosthesis—have been developed. Cochlear implant systems bypass the hair cells in the cochlea by presenting electrical stimulation directly to the auditory nerve fibers. Direct stimulation of the auditory nerve fibers leads to the perception of sound in the brain and at least partial restoration of hearing function. To facilitate direct stimulation of the auditory nerve fibers, an array of electrodes may be implanted in the cochlea. The electrodes form a number of stimulation channels through which electrical stimulation pulses may be applied directly to auditory nerve fibers within the cochlea.

However, in some instances, the electrode array is not properly inserted within the cochlea. For example, an inserted electrode array may become folded such that one or more of the electrodes covers one or more other electrodes. An inserted electrode array may be additionally or alternatively become flipped or otherwise misaligned within the cochlea. In some instances, ossification, malformations within the cochlea, and/or other anatomical anomalies may prevent proper insertion and/or function of an electrode array that is a part of a cochlear implant system.

Once an electrode array is implanted, it may be difficult or impossible to accurately identify the cause of electrode array malfunction. Computerized Axial Tomography ("CT") scans may be helpful in identifying such causes, but this imaging technique requires special equipment that may not be available in a clinician's office.

SUMMARY

Exemplary methods include using electrical field imaging to generate an electrical field spread curve for each of a plurality of electrodes contained within an electrode array at least partially inserted within a cochlear implant patient and generating a graphical representation of an intracochlear trajectory of the electrodes based on the electrical field spread curves.

Exemplary systems include a cochlear prosthesis configured to apply stimulation to at least one of a plurality of electrodes configured to be implanted within a cochlea of a patient and an interface device selectively and communicatively coupled to the cochlear prosthesis. The interface device is configured to direct the cochlear prosthesis to use electrical field imaging to generate an electrical field spread curve for each of the plurality of electrodes and generate a graphical representation of an intracochlear trajectory of the electrodes based on the electrical field spread curves.

BRIEF DESCRIPTION OF THE DRAWINGS

The accompanying drawings illustrate various embodiments of the principles described herein and are a part of the specification. The illustrated embodiments are merely examples and do not limit the scope of the disclosure.

FIGS. 7A and 7B show potential maps having abnormal field spread curves according to principles described herein.

Throughout the drawings, identical reference numbers designate similar, but not necessarily identical, elements.

DETAILED DESCRIPTION

Methods and systems of generating a graphical representation of an intracochlear trajectory of electrodes are described herein. In some examples, a cochlear prosthesis is configured to apply stimulation to at least one of a plurality of electrodes configured to be implanted within a cochlea of a patient. An interface device may be selectively and communicatively coupled to the cochlear prosthesis. The interface device is configured to direct the cochlear prosthesis to use electrical field imaging to generate an electrical field spread curve for each of the plurality of electrodes and generate a graphical representation of an intracochlear trajectory of the electrodes based on the electrical field spread curves. The graphical representation of the intracochlear trajectory may facilitate identification of a misaligned electrode array and/or an anatomical anomaly that may affect the performance of the cochlear prosthesis.

In the following description, for purposes of explanation, numerous specific details are set forth in order to provide a thorough understanding of the present systems and methods. It will be apparent, however, to one skilled in the art that the present systems and methods may be practiced without these specific details. Reference in the specification to "one embodiment" or "an embodiment" means that a particular feature, structure, or characteristic described in connection with the embodiment is included in at least one embodiment. The appearance of the phrase "in one embodiment" in various places in the specification are not necessarily all referring to the same embodiment.

Figure 1:
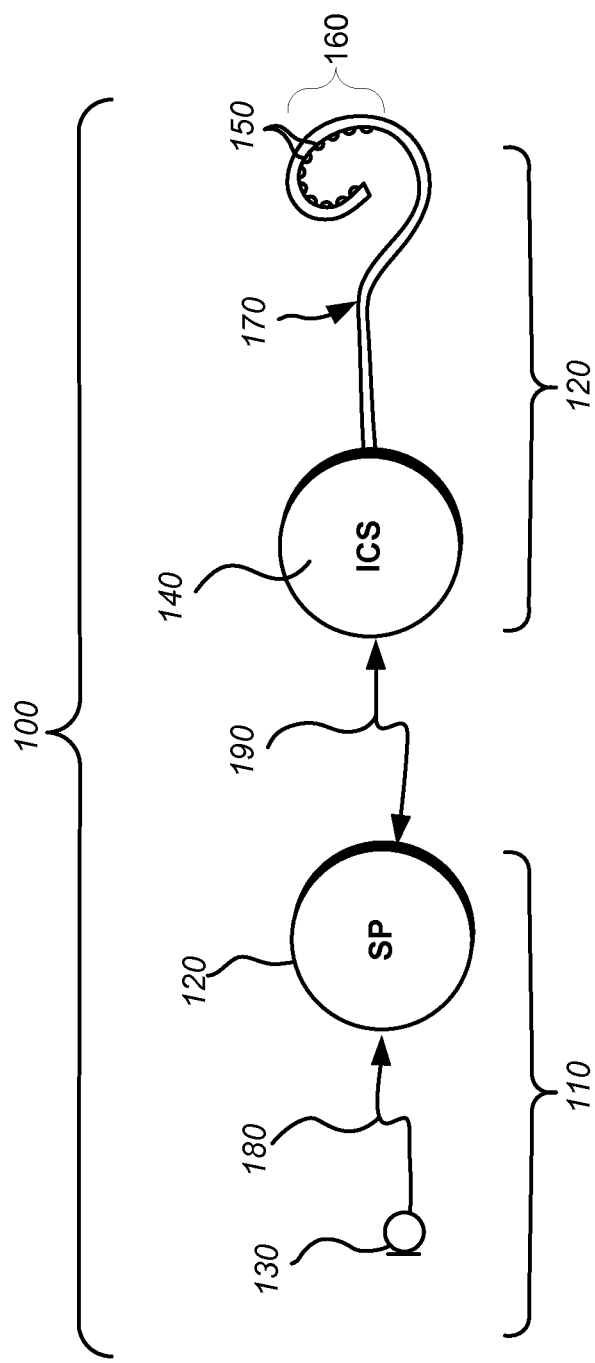
FIG. 1 illustrates an exemplary cochlear implant system according to principles described herein.

FIG. 1 illustrates an exemplary cochlear implant system 100 that may be used in accordance with the present methods and systems. The cochlear implant system 100 of FIG. 1 includes a sound processor portion 110 and a cochlear stimulation portion 120. The sound processor portion 110 may include a sound processor 120, a microphone 130, and/or additional circuitry as best serves a particular application. The cochlear stimulation portion 120 may include an implantable cochlear stimulator 140, a plurality of electrodes or electrode contacts 150 contained within an electrode array 160 disposed on a lead 170, and/or additional circuitry as best serves a particular application. The components within the sound processor portion 110 and the cochlear stimulation portion 120 will be described in more detail below.

The microphone 130 of FIG. 1 is configured to sense audio signals and convert the sensed signals to corresponding electrical signals. In some examples, the audio signal may include speech. The audio signal may additionally or alternatively include music, noise, and/or other sounds. The electrical signals are sent from the microphone 130 to the sound processor 120 via a communication link 180. Alternatively, the microphone 130 may be connected directly to, or integrated with, the sound processor 120. The sound processor 120 processes these converted audio signals in accordance with a selected sound processing strategy to generate appropriate stimulation parameters for controlling the implantable cochlear stimulator 140. These stimulation parameters may specify or define the polarity, magnitude, location (i.e., which electrode pair or electrode group receive the electrical stimulation), stimulation rate, timing (i.e., when the electrical stimulation is to be applied to a particular electrode pair), spectral tilt, and/or any other characteristic of the electrical stimulation that is generated by the implantable cochlear stimulator 140.

The lead 170 shown in FIG. 1 is configured to be inserted within a duct of a cochlea. As shown in FIG. 1, the lead 170 includes a plurality of electrodes 150, e.g., sixteen electrodes, spaced along its length. It will be understood, however, that any number of electrodes 150 may be disposed on the lead 170. Electronic circuitry within the implantable cochlear stimulator 140 is configured to generate and apply electrical stimulation to one or more stimulation sites within the cochlea via selected stimulation channels (i.e., pairs or groups of the individual electrodes 150) in accordance with a specified stimulation strategy defined by the sound processor 120.

The implantable cochlear stimulator 140 and the sound processor 120 may be communicatively coupled via a suitable data or communication link 190. It will be understood that the data communication link 190 may include a bi-directional communication link and/or one or more dedicated unidirectional communication links.

In some examples, the sound processor 120 and the microphone 130 comprise an external portion of the cochlear implant system 100 and the implantable cochlear stimulator 140 and the electrode lead 170 comprise an implantable portion of the system 100 that is implanted within a patient's body. In alternative embodiments, one or more portions of the sound processor 120 are included within the implantable portion of the cochlear implant system 100.

The external and implantable portions of the cochlear implant system 100 may each include one or more coils configured to transmit and receive power and/or control signals via the communication link 190. For example, the external portion of the cochlear implant system 100 may include an external coil (not shown) and the implantable portion of the cochlear implant system 100 may include an implantable coil (not shown). The external coil and the implantable coil may be inductively coupled to each other, thereby allowing data to be transmitted therebetween. The data may include, for example, the magnitude and polarity of a sensed audio signal. The external coil may also transmit power from the external portion to the implantable portion of the cochlear implant system 100.

It will be noted that, in some embodiments, both the sound processor 120 and the implantable cochlear stimulator 140 may be implanted within the patient, either in the same housing or in separate housings. If the sound processor 120 and the implantable cochlear stimulator 140 are in the same housing, the communication link 190 may be realized with a direct wire connection within such housing. If the sound processor 120 and the implantable cochlear stimulator 140 are in separate housings, the communication link 190 may include one or more inductive links, for example.

Figure 2:
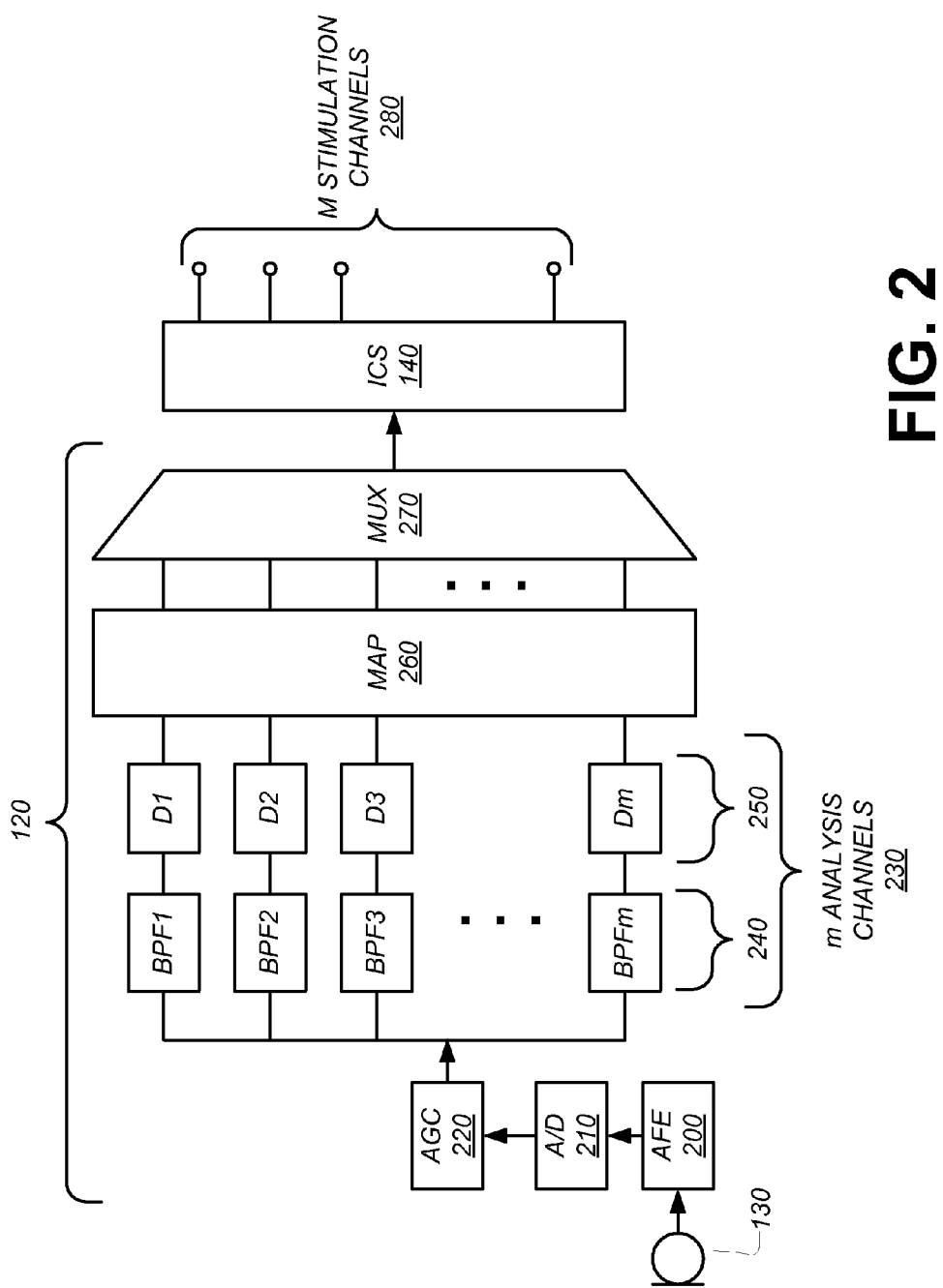
FIG. 2 is a functional block diagram of an exemplary sound processor and implantable cochlear stimulator according to principles described herein.

FIG. 2 is a functional block diagram of an exemplary sound processor 120 and implantable cochlear stimulator 140. The functions shown in FIG. 2 are merely representative of the many different functions that may be performed by the sound processor 120 and/or the implantable cochlear stimulator 140.

As shown in FIG. 2, the microphone 130 senses an audio signal, such as speech or music, and converts the audio signal into one or more electrical signals. These signals are then amplified in audio front-end (AFE) circuitry 200. The amplified audio signal is then converted to a digital signal by an analog-to-digital (A/D) converter 210. The resulting digital signal is then subjected to automatic gain control using a suitable automatic gain control (AGC) function 220.

After appropriate automatic gain control, the digital signal is then processed in one of a number of digital signal processing or analysis channels 230. For example, the sound processor 120 may include, but is not limited to, eight analysis channels 230. Each analysis channel 230 may respond to a different frequency band of the sensed audio signal due to a series of band pass filters 240.

As shown in FIG. 2, each of the m analysis channels 230 may also include an energy detection stage (D1-Dm) 250. Each energy detection stage 250 may include any combination of circuitry configured to detect the amount of energy contained within each of the m analysis channels 230. For example, each energy detection stage 250 may include a rectification circuit followed by an integrator circuit.

After energy detection, the signals within each of the m analysis channels 230 are forwarded to a mapping stage 260. The mapping stage 260 is configured to map the signals in each of the m analysis channels 230 to one or more of M stimulation channels 280. In other words, the information contained in the m analysis channels 230 is used to define the electrical stimulation pulses that are applied to the patient by the implantable cochlear stimulator 140 via the M stimulation channels 280. As mentioned previously, pairs or groups of individual electrodes 150 may make up the M stimulation channels 280.

In some examples, the mapped signals are serialized by a multiplexer 270 and transmitted to the implantable cochlear stimulator 140. The implantable cochlear stimulator 140 may then apply electrical stimulation via one or more of the M stimulation channels 280 to one or more stimulation sites within the duct of the patient's cochlea. As used herein, the term "stimulation site" will be used to refer to a target area or location to which the electrical stimulation is applied. For example, a stimulation site may refer to any location within a region of auditory nerve tissue shown in FIG. 3.

Figure 3:
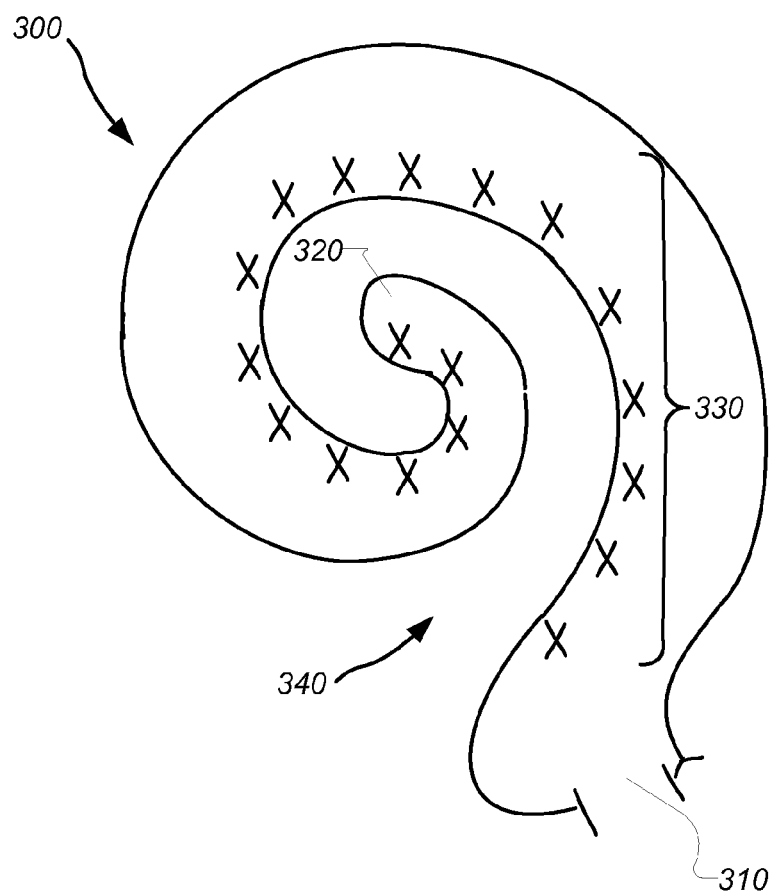
FIG. 3 illustrates a schematic structure of the human cochlea highlighting elements according to principles described herein.

FIG. 3 illustrates a schematic structure of the human cochlea 300. As shown in FIG. 3, the cochlea 300 is in the shape of a spiral beginning at a base 310 and ending at an apex 320. Within the cochlea 300 resides auditory nerve tissue 330, which is denoted by Xs in FIG. 3. The auditory nerve tissue 330 is organized within the cochlea 300 in a tonotopic manner. Low frequencies are encoded at the apex 320 of the cochlea 300 while high frequencies are encoded at the base 310. Hence, each location along the length of the cochlea 300 corresponds to a different perceived frequency. A cochlear prosthesis, such as cochlear implant system 100, may therefore be implanted within a patient with sensorineural hearing loss and configured to apply electrical stimulation to different locations within the cochlea 300 to provide the sensation of hearing.

To this end, a lead 170 with an electrode array 160 disposed thereon may be implanted within a duct 340 of the cochlea 300 in order to facilitate electrical stimulation of one or more stimulation sites within the cochlea 300. During an implant procedure, a surgeon may attempt to position the electrode array 160 such that individual electrode contacts 150 are appropriately distributed within the cochlea. However, because of the shape of the cochlea 300 and the small size of the electrode array 160, it is often difficult to optimally position an electrode array 160 within the cochlea 300.

Improper positioning of an electrode array 160 within the cochlea 300 often results in sub-optimal performance by a cochlear implant system 100. For example, an electrode array 160 that is folded, flipped, or otherwise misaligned may result in inappropriately mapped frequencies, the patient perceiving the same pitch when electrical stimulation is applied via different electrodes 150, and/or complete prosthetic malfunction.

Moreover, anatomical anomalies may result in sub-optimal performance by a cochlear implant system 100, even in cases where the electrodes 150 have been appropriately positioned within the cochlea 300. For example, ossification within the cochlea 300 may result in skewed pitches and/or loss in sound quality. Other malformations may similarly affect the performance of a cochlear implant system 100.

Hence, it is desirable to ensure proper electrode positioning and function during initial implantation of the electrodes 150, when the cochlear implant system 100 is fitted to the patient, and/or during follow-up checks thereafter. To this end, the methods and systems described herein facilitate both intraoperative and postoperative analysis of electrode positioning and function. As will be described herein, a graphical representation of an intracochlear trajectory of individual electrodes 150 inserted within the cochlea 300 may be provided for display. The graphical representation may be used by a surgeon, clinician, or other user to determine whether the electrodes 150 need to be repositioned during surgery and/or whether the stimulation parameters need to be adjusted during fitting and/or during follow-up checks thereafter. As used herein, "intracochlear trajectory" refers to a path or location of the electrodes 150 in relation to one another. Exemplary intracochlear trajectories will be described in more detail below.

Figure 4:
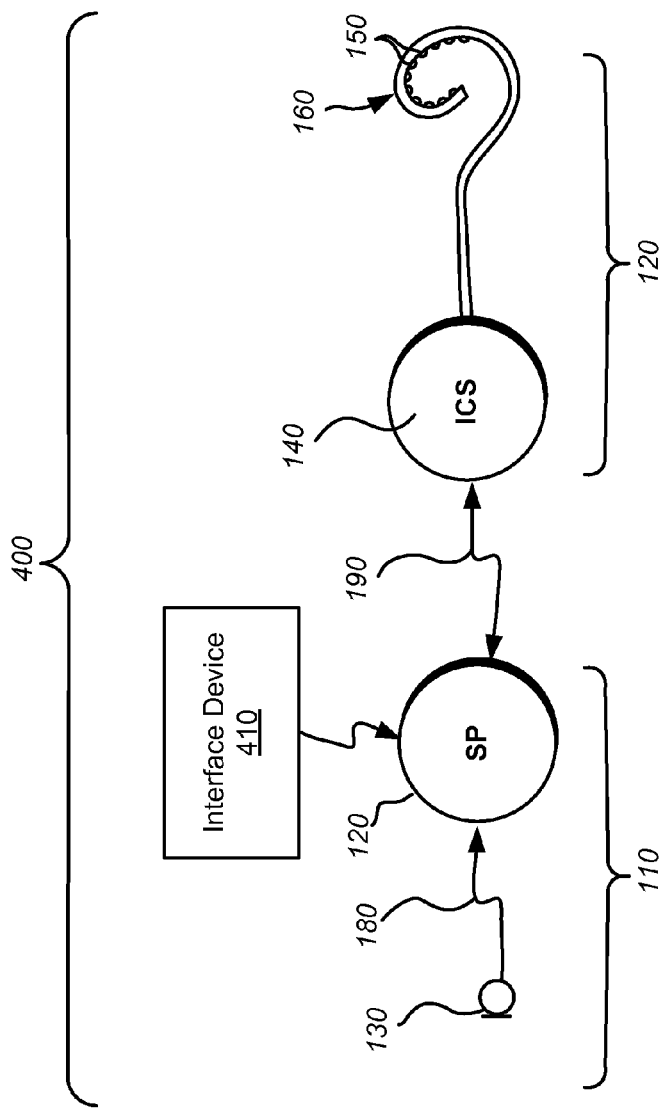
FIG. 4 illustrates an exemplary system configured to facilitate analysis of electrode positioning and function according to principles described herein.

FIG. 4 illustrates an exemplary system 400 configured to facilitate analysis of electrode positioning and function. As shown in FIG. 4, an interface device 410 may be selectively and communicatively coupled to the sound processor 120. The interface device 410 may include any combination of hardware, software, and firmware configured to perform any of the functions described herein. For example, the interface device 410 may include a fitting station, personal computer, handheld device (e.g., a personal digital assistant), a mobile device (e.g., a mobile telephone), and/or any other electronic device as may serve a particular application. As will be described in more detail below, the interface device 410 may be configured to direct cochlear implant system 100 to perform electrical field imaging ("EFI"). The interface device 410 may then display a graphical representation of the intracochlear trajectory of electrodes 150 located within the cochlea 300 based on the electrical field imaging.

Figure 5:
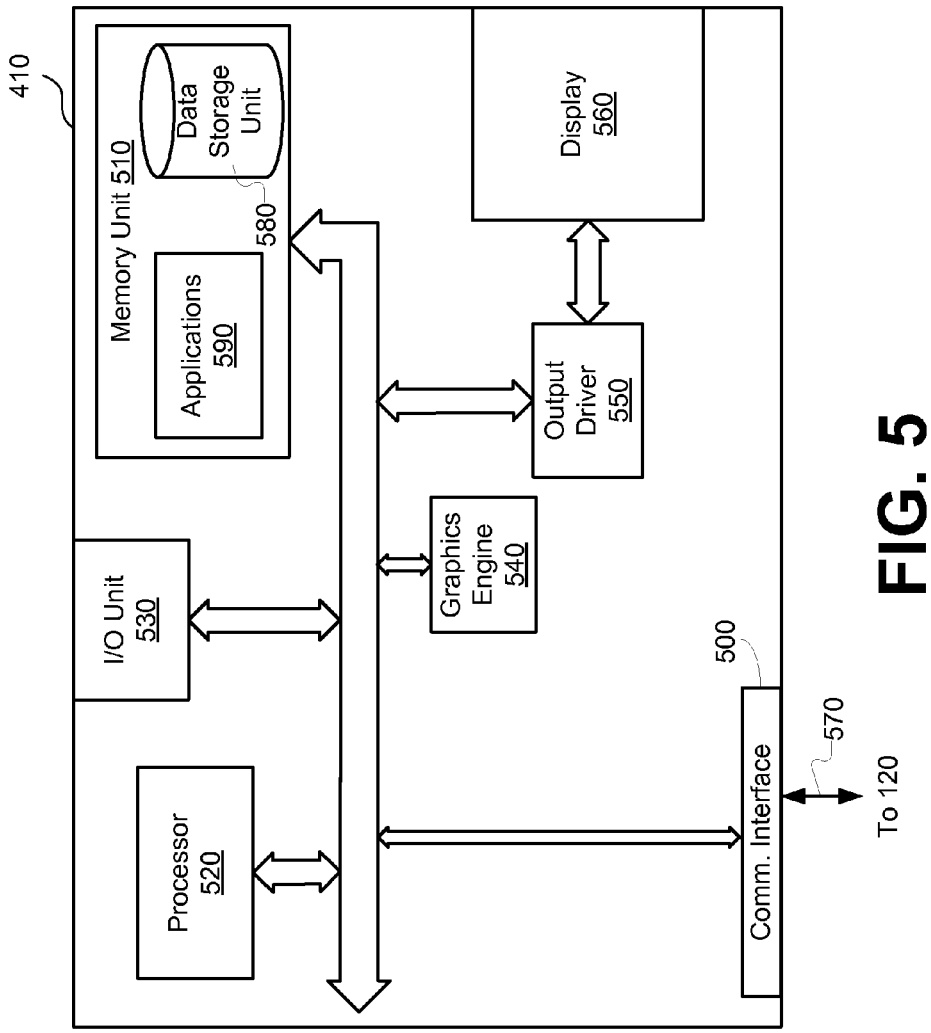
FIG. 5 illustrates a number of components that may be included within an exemplary interface device according to principles described herein.

FIG. 5 illustrates a number of components that may be included within an exemplary interface device 410. While an exemplary interface device 410 is shown in FIG. 5, the exemplary components illustrated in FIG. 5 are not intended to be limiting. Indeed, additional or alternative components and/or implementations may be included within the interface device 410.

In general, the interface device 410 may include any device configured to be selectively and communicatively coupled to one or more components of the cochlear implant system 100. For example, the interface device 410 may be selectively and communicatively coupled to the sound processor 120. Interface device 410 may also be configured to interact with various peripherals such as a terminal, keyboard, mouse, display screen, printer, stylus, input device(s), output device(s), and/ or any other apparatus(es).

As shown in FIG. 5, the interface device 410 may include a communication interface 500, programmable memory unit 510, processor 520, input/output unit 530 ("I/O unit 530"), graphics engine 540, output driver 550, and display 560 communicatively connected to one another.

Communication interface 500 may be configured to transmit to and receive data from the sound processor 120. Exemplary data transmitted from the interface device 410 to the sound processor 120 includes interface commands, programming data, etc. Exemplary data received by the interface device 410 from the sound processor 120 includes electrical field imaging data.

In some examples, a communications link 570 may be used to facilitate communication between the interface device 410 and the sound processor 120. The communications link 570 may include any type of link used to transmit data, such as, but not limited to, an RF link, an infrared (IR) link, an optical link, a Bluetooth link, a network link, a thermal link, a wire link, or any other suitable link. In some alternative examples, data acquired by the sound processor 120 may be saved onto a data storage medium (e.g., a flash drive, hard drive, optical disk, etc.) and later read by interface device 410.

Programmable memory unit 510 may include, but is not limited to, FLASH memory, RAM, DRAM, or a combination thereof. The programmable memory unit 510 may additionally or alternatively include a data storage unit 580. The data storage unit 580 may include one or more data storage media, devices, or configurations and may employ any type, form, and combination of storage media. For example, the data storage unit 580 may include, but is not limited to, a hard drive, flash drive, optical disk, or other non-volatile storage unit. Log data resulting from electrical field imaging performed by the cochlear implant system 100 may be stored within the data storage unit 580.

Processor 520 may be configured to control one or more operations of the components included within the interface device 410. Processor 520 may direct execution of operations in accordance with computer-executable instructions such as may be stored in memory unit 510. As an example, processor 520 may be configured to process electrical field imaging data and generate an intracochlear trajectory of electrodes 150 accordingly.

I/O unit 530 may be configured to receive user input and provide user output and may include any hardware, firmware, software, or combination thereof supportive of input and output capabilities.

As instructed by processor 520, graphics engine 540 may generate graphics, which may include graphical user interfaces ("GUIs"). The output driver 550 may provide output signals representative of the graphics generated by graphics engine 540 to display 560. The display 560 may then present the graphics to the user.

One or more applications 590 may be executed by the interface device 410. The applications, or application clients, may reside in memory unit 510 or in any other area of the interface device 410 and be executed by the processor 520. Each application 590 may correspond to a particular feature or capability of the interface device 410. For example, illustrative applications 590 may include one or more of a GUI application and a data processing application.

It will be recognized that one or more processes and/or applications described herein may be implemented at least in part as computer-executable instructions, i.e., instructions executable by one or more computing devices, tangibly embodied in a computer-readable medium. In general, a processor (e.g., a microprocessor) receives instructions, e.g., from a memory, a computer-readable medium, etc., and executes those instructions, thereby performing one or more processes, including one or more of the processes described herein. Such instructions may be stored and transmitted using a variety of known computer-readable media.

A computer-readable medium (also referred to as a processor-readable medium) includes any medium that participates in providing data (e.g., instructions) that may be read by a computer (e.g., by a processor of a computer). Such a medium may take many forms, including, but not limited to, non-volatile media, volatile media, and transmission media. Non-volatile media may include, for example, optical or magnetic disks and other persistent memory. Volatile media may include, for example, DRAM, which typically constitutes a main memory. Transmission media may include, for example, coaxial cables, copper wire and fiber optics, including the wires that comprise a system bus coupled to a processor of a computer. Transmission media may include or convey acoustic waves, light waves, and electromagnetic emissions, such as those generated during RF and infrared IR data communications. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH-EEPROM, any other memory chip or cartridge, or any other medium from which a computer can read.

As mentioned, interface device 410 may be configured to direct the cochlear implant system 100 to perform electrical field imaging. In electrical field imaging, an intracochlear potential (also referred to herein as "voltage") map is derived by consecutive stimulation of each electrode contact 150 (e.g., from apex to base). Each time electrical stimulation is applied to one of the electrode contacts 150, the intracochlear potential is measured at all of the electrode contacts 150 such that a complete potential profile along the cochlea 300 is obtained.

Figure 6:
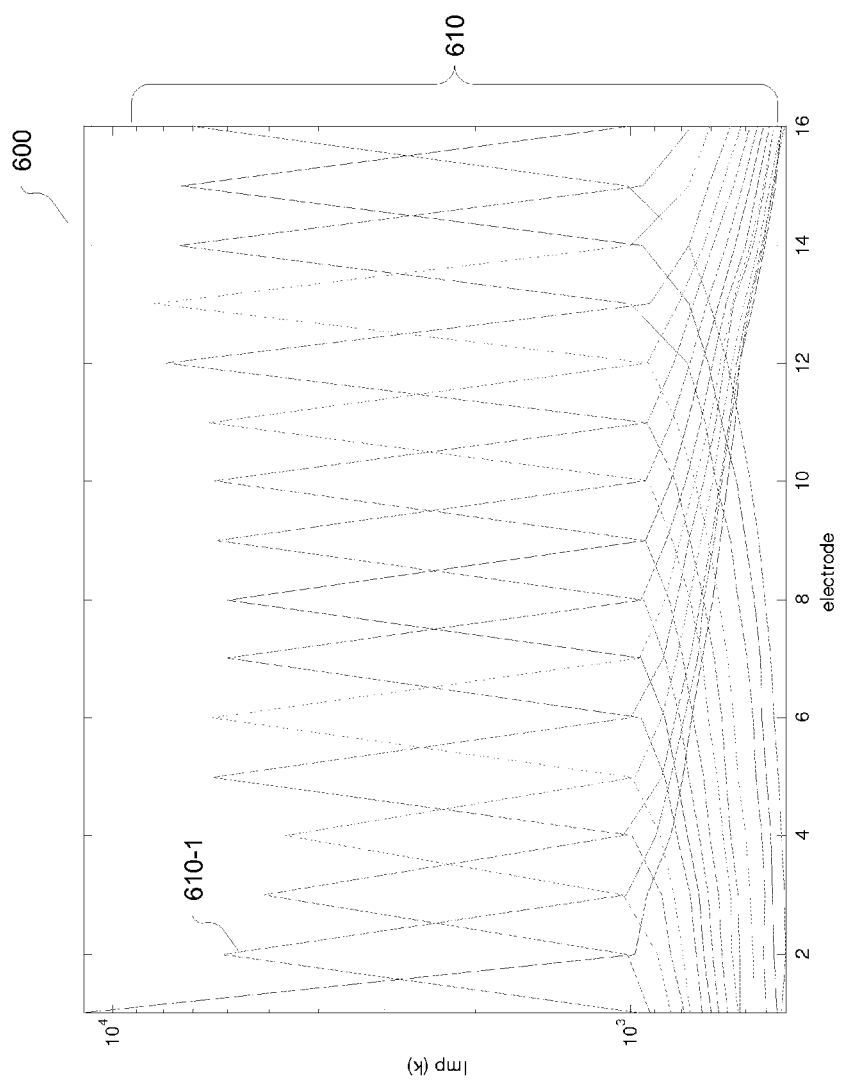
FIG. 6 shows an exemplary intracochlear potential map for an array of sixteen electrodes that may be derived by electrical field imaging according to principles described herein.

To illustrate, FIG. 6 shows an exemplary intracochlear potential map 600 for an array of sixteen electrodes 150 that may be derived by electrical field imaging. The map 600 corresponds to a normal cochlear implant patient with a properly functioning electrode array 160. It will be recognized that the electrode array 160 may include any number of electrodes 150 as may serve a particular application.

As shown in FIG. 6, map 600 includes a plurality of electrical field spread curves 610. Each field spread curve 610 may be generated by stimulating one of the intracochlear electrodes 150. For example, field spread curve 610-1 is generated by stimulating a second electrode 150 within the electrode array 160. In other words, field spread curve 610-1 represents a voltage as measured by each electrode 150 when stimulation current is applied to the second electrode 150. The stimulation current may be applied in accordance with any suitable stimulation parameter. For example, the stimulation current may include relatively low amplitude sinusoidal pulses having a relatively high frequency (e.g., 3 to 6 kHz). The frequency range is merely illustrative and may be varied as may serve a particular applicant. This type of measurement may be referred to as a frequency domain measurement. Additionally or alternatively, a measurement in the time domain may be performed, e.g. with a biphasic current pulse.

The resultant voltages may be divided by the applied stimulation current for normalization purposes. They are therefore represented in FIG. 6 in terms of impedance (Ohms). Because voltage and impedance are directly proportional, an increase in impedance corresponds to an increase in voltage. Likewise, a decrease in impedance corresponds to a decrease in voltage. Hence, the terms "voltage" and "impedance" will be used interchangeably herein.

When a particular electrode 150 is stimulated, the maximum recorded voltage occurs at the physical location of that electrode 150. This is illustrated by the peaks within the field spread curves 610. As shown in FIG. 6, the measured voltages decay as a function of distance from the stimulated electrode 150.

The field spread curves 610 may be represented mathematically by a voltage matrix Z. Voltage matrix Z may be interchangeably referred to herein as "impedance matrix Z". As will be described in more detail below, the impedance matrix Z may be used to derive a "distance matrix" configured to represent relative electrical distances between all electrodes 150 within an electrode array 160.

Figure 7A:
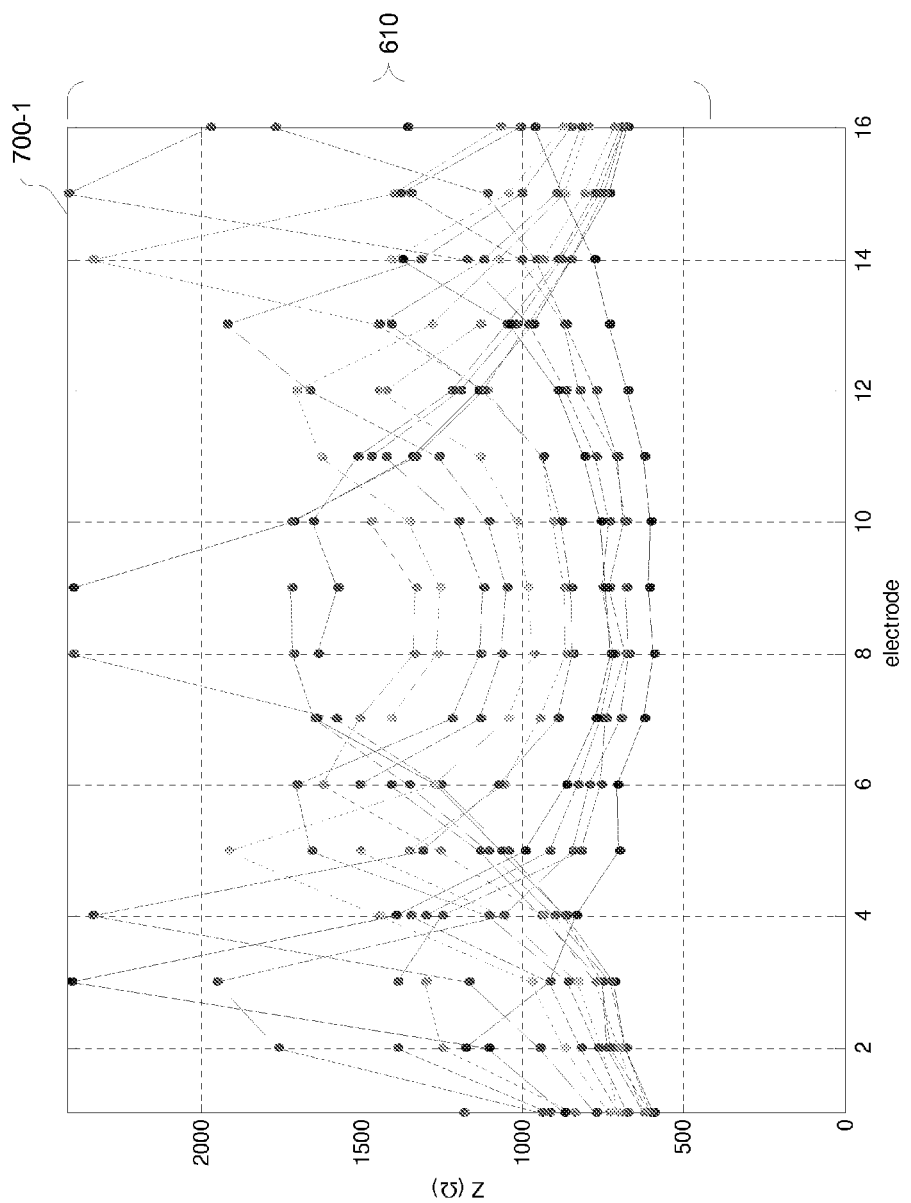

As mentioned, the potential map 600 shown in FIG. 6 is representative of a properly functioning electrode array 160 appropriately positioned within the cochlea 300 of a normal patient. Improper positioning of an electrode array 160 and/or one or more anatomical anomalies may result in abnormal or skewed field spread curves 610. For example, FIGS. 7A and 7B show potential maps 700-1 and 700-2 (referred to herein as "abnormal potential maps 700") having abnormal field spread curves 610. Abnormal potential map 700-1 includes field spread curves 610 that are non-monotonous lacking in symmetry. Abnormal potential map 700-2 includes some field spread curves 610 having abnormally low peaks. It will be recognized that potential maps 700-1 and 700-2 are merely illustrative of the many different potential maps 700 that may be abnormal in nature.

In some examples, interface device 410 may be configured to display a graphical representation of an intracochlear potential map 600 for viewing by a surgeon, clinician, or other. However, interpretation of abnormal potential maps (e.g., 700-1 and 700-2) can be difficult or even impossible. For example, it may be difficult or impossible for a surgeon or clinician to determine the cause of an abnormal potential map 700 by merely viewing the abnormal map 700.

Hence, in some examples, interface device 410 may be configured to use the potential maps 600 produced by electrical field imaging to generate a graphical interface that readily conveys information representative of electrode position and performance. To this end, interface device 410 may be configured to derive a distance matrix (also referred to herein as a $\Delta Z$ matrix) from the impedance matrix Z. The principle is that electrodes that are physically close together also have similar electrical characteristics. The electrical distance between an electrode i and j may therefore be defined as a function of the voltages $Z(i,j)$ and $Z(i,i)$, belonging to the field spread curve of electrode i; i.e. $\Delta Z(i,j)=fun(Z(i,j),Z(i,i))$. One example of such distance function is $\Delta Z(i,j)=abs(Z(i,j)-Z(i,i))$ for each (i,j) electrode pair. In other words, an electrical distance between two electrodes 150 within an electrode array 160 may be represented by a difference in impedance between the two electrodes 150 when stimulation current is applied to one of the electrodes 150. Other distance functions are conceivable as well. In some examples, a transformation of the voltage $Z(i,i)$ may be necessary to only include the voltage in the cochlear tissue and eliminate the electrode contact impedance contribution. As an example $Z(i,i)$ may be replaced with an extrapolated value.

Figure 8:
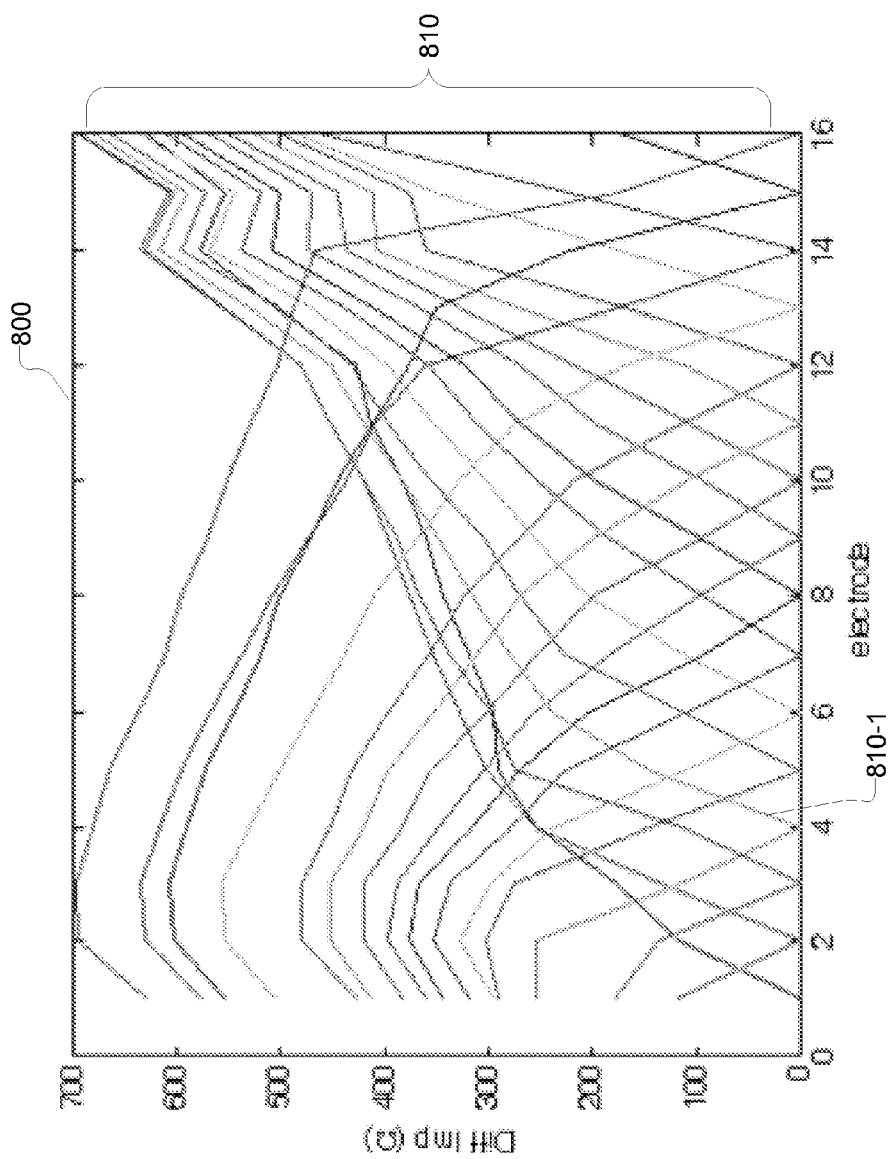
FIG. 8 is a graphical representation of an exemplary distance matrix corresponding to a properly functioning electrode array appropriately positioned within the cochlea of a normal patient according to principles described herein.

FIG. 8 is a graphical representation 800 of an exemplary distance matrix corresponding to a properly functioning electrode array 160 appropriately positioned within the cochlea 300 of a normal patient. As shown in FIG. 8, the graphical representation 800 may include a $\Delta Z$ distance line 810 corresponding to each electrode 150. For example, $\Delta Z$ distance line 810-1 corresponds to a fourth electrode 150 within the electrode array 160 and shows that the change in impedance, or electrical distance, increases as a function of distance from the electrode 150.

In some examples, interface device 410 may perform one or more operations on the distance matrix to generate and display a graphical representation of an intracochlear trajectory of the electrodes 150. For example, interface device 410 may be configured to apply a multidimensional scaling algorithm to the distance matrix. The role of the multidimensional scaling algorithm is to find the set of points in N-dimensional space whose pairwise distances approximate best the values in the given distance matrix $\Delta Z$. This set of points constitutes a graphical representation of an intracochlear trajectory of the electrodes 150. The intracochlear trajectory may be represented in any suitable dimension as may serve a particular application. For example, the intracochlear trajectory of the electrodes 10 may be represented in two or three dimensional space. For illustrative purposes, the intracochlear trajectories described herein are in two dimensional space. While the operations described herein are performed by interface device 410, it will be recognized that any other component of the cochlear implant system 100 (e.g., the sound processor 120) may be configured to perform one or more of the operations.

An exemplary multidimensional scaling algorithm that may be used to generate an intracochlear trajectory of electrodes 150 will now be described. However, it will be recognized that interface device 410 may generate a graphical representation of an intracochlear trajectory of electrodes 150 using any other algorithm, technique, or heuristic.

In a first step, classical multidimensional scaling or principal component analysis may be performed on the distance matrix. Principal component analysis is a statistical technique used to derive a number of functions that, when summed together, describe a given set of data. These functions are often referred to as basis functions or principal components, both of which terms will be used interchangeably herein. The outcome of the classical multidimensional scaling step is a matrix P whose columns contain the principal components. Only as many columns are retained as the dimensionality of the space (e.g. 2 for 2-D space). The rows of the reduced P matrix constitute an initial set of points whose distances match already quite well with the given distance matrix $\Delta Z$.

A further non-linear refinement step is then performed. For example, a steepest gradient search may be performed starting from initial values. Non-linear refinement step may be performed in accordance with one or more stress criteria. For example, the non-linear refinement step may be performed in accordance with a goodness-of-fit metric such as Kruskall's stress1 criterion, which may be represented by $S=\sqrt{((\Sigma_i \Sigma_{j>i}(dist(i,j)-\Delta Z(i,j))^2)/(\Sigma_i \rho_{j>i}(dist(i,j)^2))}$. The non-linear refinement step may additionally or alternatively be performed in accordance with a metric stress criterion, which may be represented by $M=\sqrt{((\Sigma_i \Sigma_{j>i}(dist(i,j)-\Delta Z(i,j))^2)/(\Sigma_i \Sigma_{j>i} \Delta Z(i,j)^2))}$. In both of these equations, dist(i,j) equals the Eucledian distance between point i and point j (at iteration). The stress criteria can be further refined, e.g. to include weighting coefficients.

Figure 9:
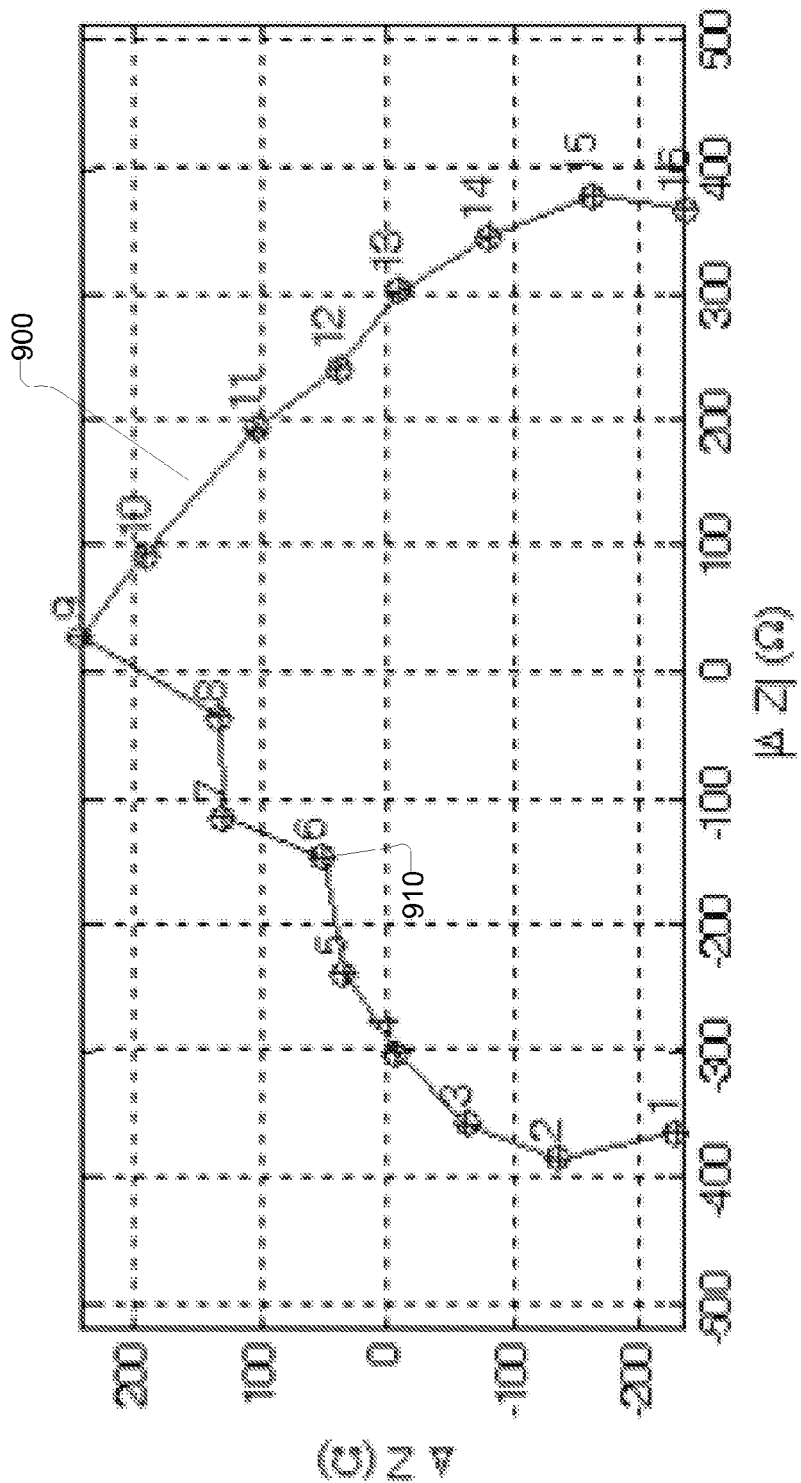
FIG. 9 illustrates an exemplary graphical representation of an intracochlear trajectory of electrodes according to principles described herein.

FIG. 9 illustrates an exemplary graphical representation of an intracochlear trajectory 900 of electrodes 150 corresponding to a properly functioning electrode array 160 appropriately positioned within the cochlea 300 of a normal patient. As shown in FIG. 9, both the horizontal and vertical axes are measured in terms of $\Delta Z$, or electrical distance. Each dot (e.g., dot 910) represents a particular electrode 150 within an electrode array 160. Hence, the intracochlear trajectory 900 shown in FIG. 9 depicts a path or location of the electrodes 150 in relation to one another. For example, FIG. 9 shows that electrodes 1 and 2 are located relatively close to one another, while electrodes 1 and 9 are located relatively far away from one another.

Hence, a graphical representation of an intracochlear trajectory 900 may provide an intuitive and accurate means of identifying whether the electrodes 150 are properly positioned within the cochlea and/or whether one or more anatomical anomalies exist within the patient that affect the performance of the cochlear implant system 100. It will be recognized that the absolute location of the dots in the space carries no meaning. The graphical representation can rotated, shifted or mirrored. Only the relative distances of the dots carry meaning.

Figure 10:
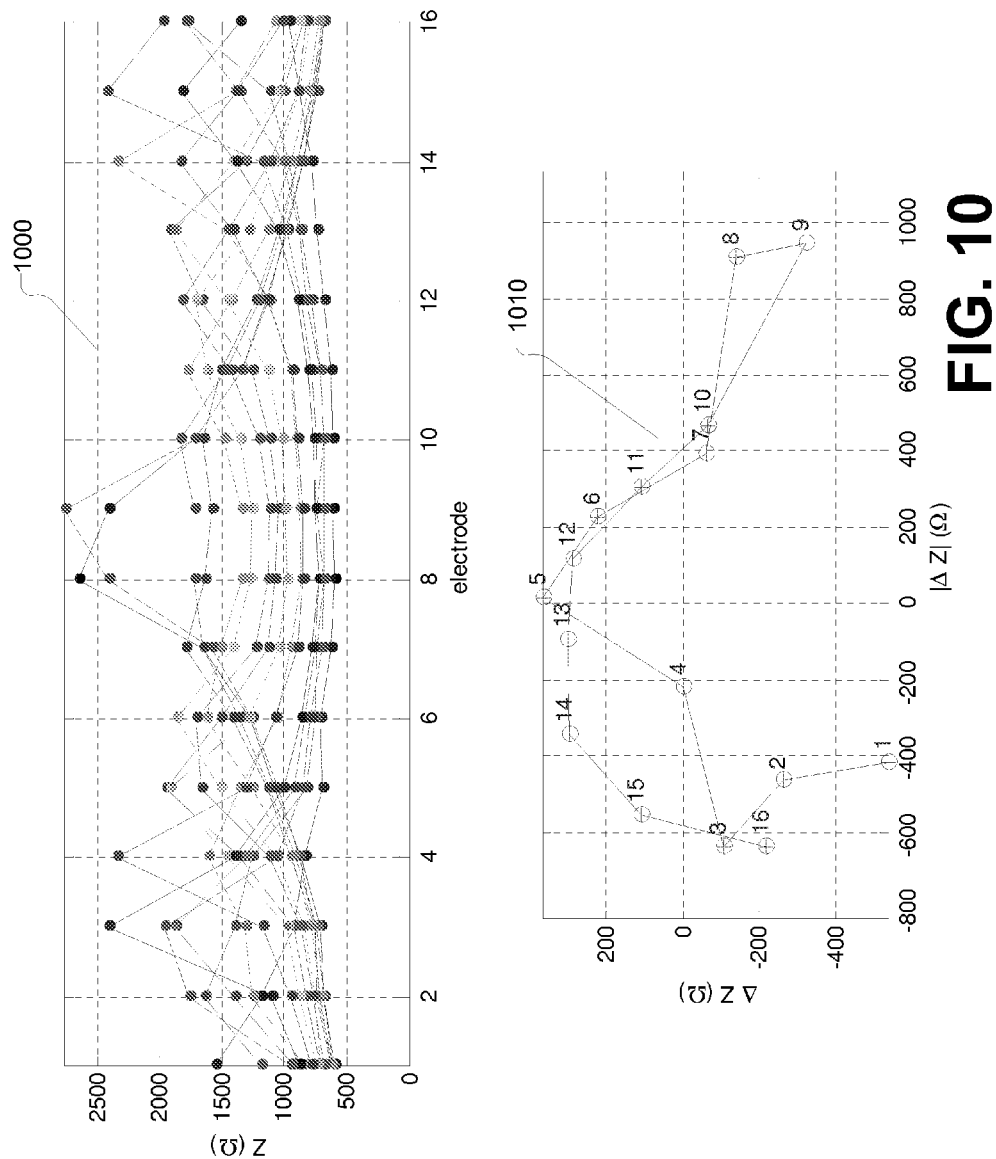
FIG. 10 shows an abnormal potential map and its corresponding intracochlear trajectory according to principles described herein.

For example, FIG. 10 shows an abnormal potential map 1000 and its corresponding intracochlear trajectory 1010 that may be acquired for a patient experiencing difficulties with a cochlear implant system 100. While a clinician may recognize that potential map 1000 is abnormal, it may be difficult or impossible for the clinician to recognize the cause of the abnormality. However, by analyzing the corresponding intracochlear trajectory 1010, the clinician may readily recognize that electrodes 12 through 16 are atypically located in a region similar to that of electrodes 1 through 5. Hence, the intracochlear trajectory 1010 shows that the electrode array 160 is folded over. The intracochlear trajectory 1010 may also be used to determine that electrodes 7 and 10, for example, are positioned closely together, thus resulting in similar pitches being perceived by the patient when stimulation current is applied to these electrodes.

A CT scan of the patient associated with the graphics in FIG. 10 and an analysis of feedback provided by the patient verify the information conveyed by intracochlear trajectory 1010. In this instance, a CT scan showed that the electrode array 160 was folded over in the first ¾ of the basal turn. The patient also reported no difference between a fitting with electrodes 9 to 16 enabled and one with electrodes 1-8 enabled (reverse tonotopy).

Figure 11:
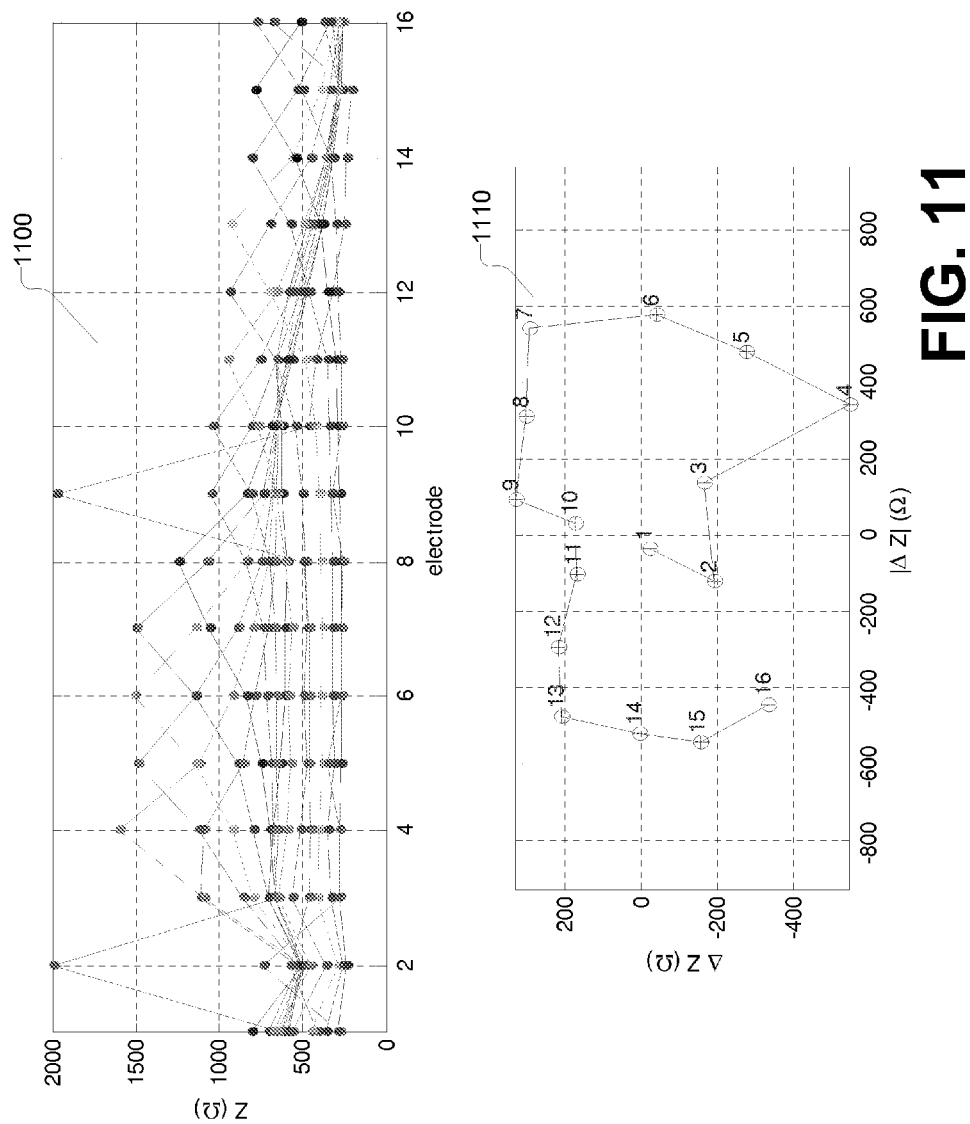
FIG. 11 shows another abnormal potential map and its corresponding intracochlear trajectory according to principles described herein.

FIG. 11 shows another abnormal potential map 1100 and its corresponding intracochlear trajectory 1110 that may be acquired for another patient experiencing difficulties with a cochlear implant system 100. By analyzing the corresponding intracochlear trajectory 1010, the clinician may readily recognize that one or more electrodes 150 are atypically located relative one to another. Hence, the intracochlear trajectory 1010 shows that the some of the electrodes 150 have not been properly inserted into the cochlea. Indeed, a CT scan of the patient configured that the cochleostomy was located at the second turn of the cochlea and opened up towards the first turn of the cochlea. The electrode array 160 passed right next to the modiolus and then followed a normal trajectory. Hence, the CT scan showed that the electrode array 160 was not properly inserted into the cochlea.

Figure 12A:
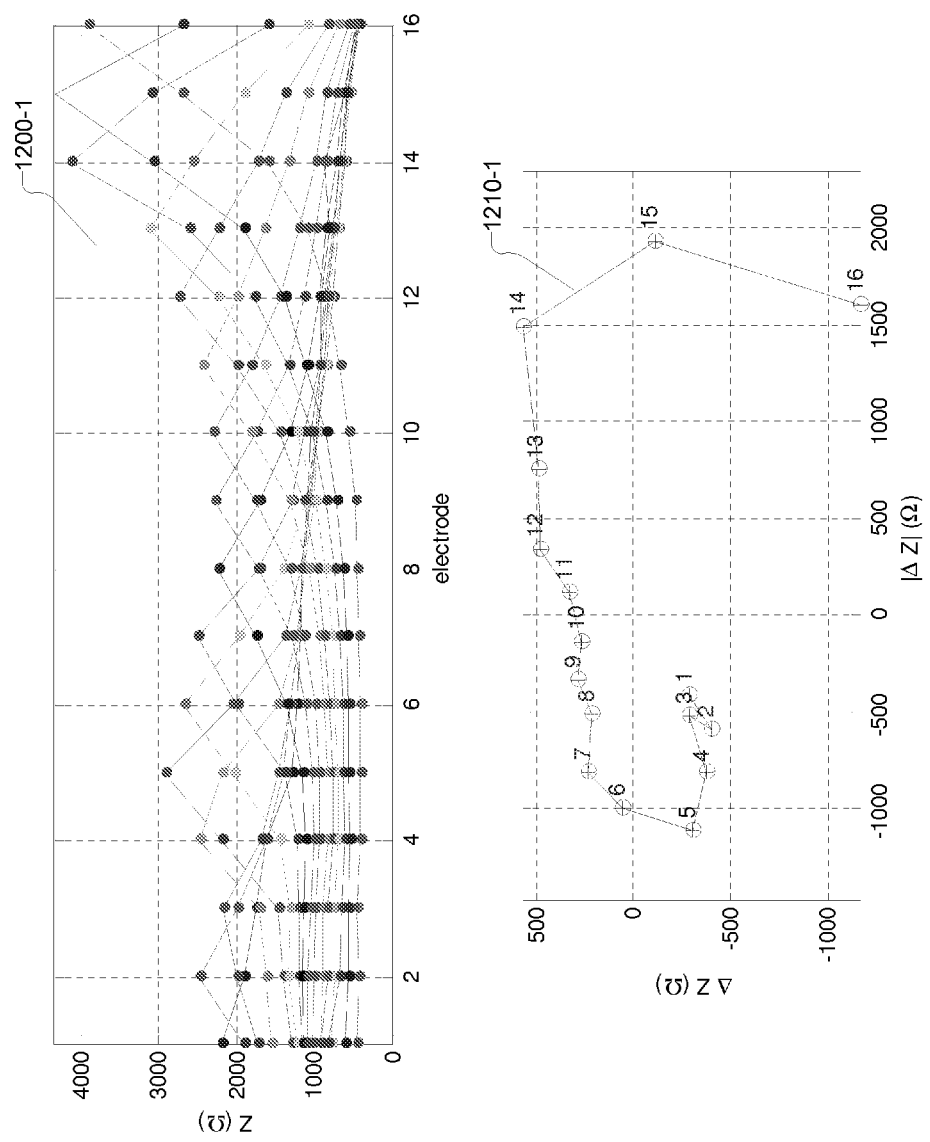
FIGS. 12A-12C show additional examples of abnormal potential maps and their corresponding intracochlear trajectories according to principles described herein.
Figure 12B:
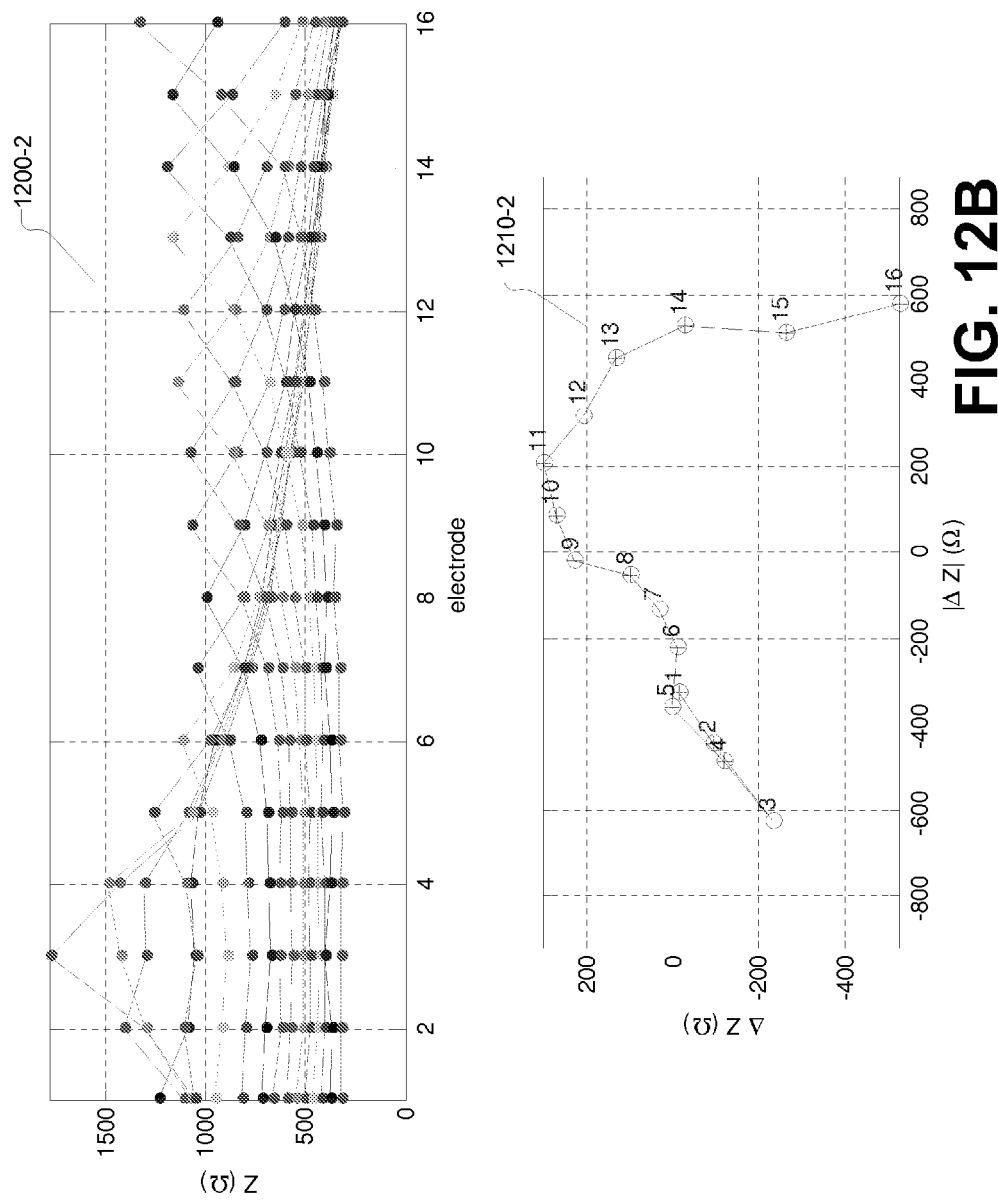
Figure 12C:
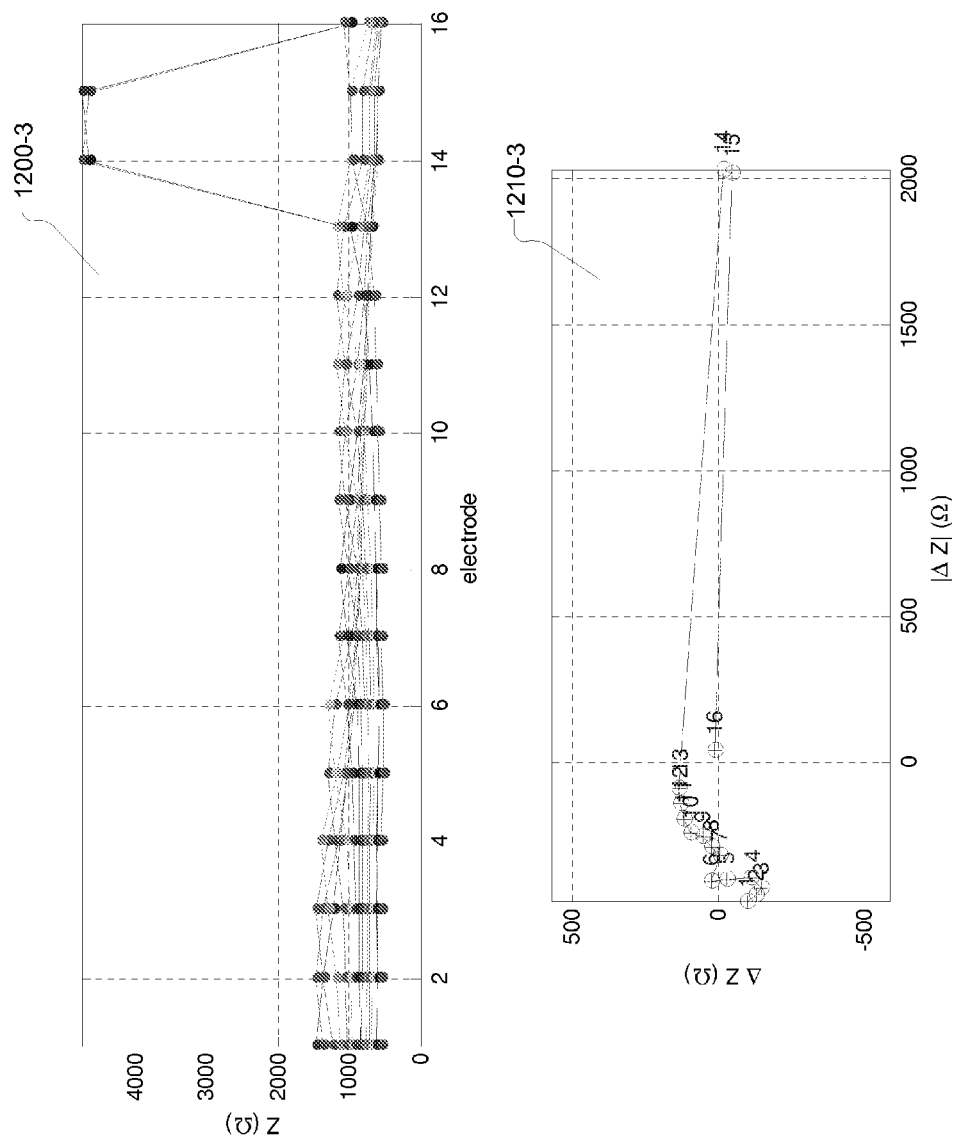

FIGS. 12A-12C show additional examples of abnormal potential maps 1200-1 through 1200-3 and their corresponding intracochlear trajectories 1210-1 through 1210-3. The abnormal potential map 1200-1 and intracochlear trajectory 1210-1 shown in FIG. 12A, for example, correspond to a situation wherein partial ossification has occurred at the basal end of the cochlea. The abnormal potential map 1200-2 and intracochlear trajectory 1210-2 shown in FIG. 12B correspond to a situation wherein a tip of the electrode array 160 containing electrodes 1 through 5 has been flipped. The abnormal potential map 1200-3 and intracochlear trajectory 1210-3 shown in FIG. 12C correspond to a situation wherein a short circuit within one or more of the electrodes 150 has occurred.

It will be recognized that the systems and methods described herein may be modified and/or varied as may serve a particular application. For example, the distance matrix may be augmented to include the impedance difference with respect to the reference electrode. For example, if the electrode array 160 includes 16 electrodes 150, the distance matrix may be a 17×17 matrix where $\Delta Z(17,j)=Z(j,j)$. Additionally or alternatively, the topology of the intracochlear trajectories described herein may be shifted, rotated, or mirrored without affecting distances. Hence, a reference electrode 150 may correspond to the origin (0,0), and the intracochlear trajectory may be rotated such that the vertical axis points to the centroid of electrodes 1-16. It may be mirrored if needed such that the first electrode 150 is more "left" than the last electrode 150 in the electrode array 160.

Figure 13:
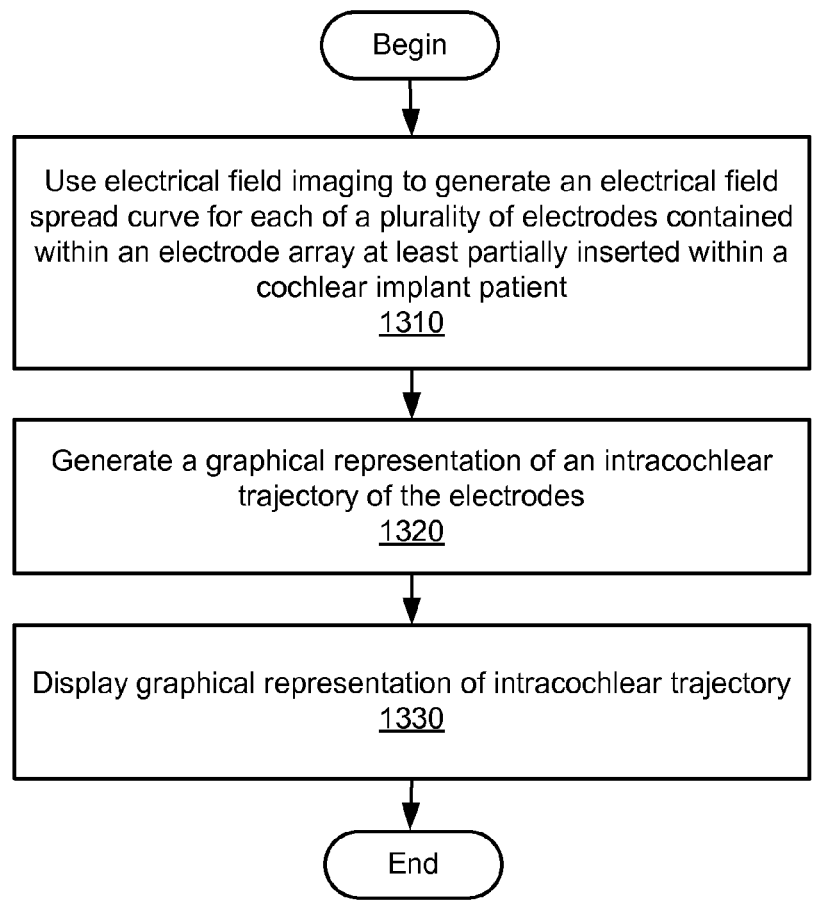
FIG. 13 illustrates an exemplary method of generating a graphical representation of an intracochlear trajectory of electrodes contained within an intracochlear electrode array according to principles described herein.

FIG. 13 illustrates an exemplary method of generating a graphical representation of an intracochlear trajectory of electrodes contained within an intracochlear electrode array. While FIG. 13 illustrates exemplary steps according to one embodiment, other embodiments may omit, add to, reorder, and/or modify any of the steps shown in FIG. 13. Any of the steps described in FIG. 13 may be performed by interface device 410, sound processor 120, implantable cochlear stimulator 140, and/or any other component included within system 400 as may serve a particular application.

In step 1310, electrical field imaging is used to generate an electrical field spread curve for each of a plurality of electrodes contained within an electrode array at least partially inserted within a cochlear implant patient. The electrical field spread curves may be generated in any of the ways described herein.

In step 1320, a graphical representation of an intracochlear trajectory of the electrodes is generated. The intracochlear trajectory may be generated in any of the ways described herein, and may be based at least on part on the electrical field spread curves.

In step 1330, the graphical representation of the intracochlear trajectory is displayed. The graphical representation of the intracochlear trajectory may be displayed in any of the ways described herein. In this manner, a clinician and/or other user may readily identify an improperly positioned electrode array and/or one or more anatomical anomalies that may affect the performance of a cochlear implant system.

The preceding description has been presented only to illustrate and describe embodiments of the invention. It is not intended to be exhaustive or to limit the invention to any precise form disclosed. Many modifications and variations are possible in light of the above teaching.

What is claimed is:

1. A method comprising:
    using electrical field imaging to generate an electrical field spread curve for each of a plurality of electrodes contained within an electrode array at least partially inserted within a cochlear implant patient;
    generating a graphical representation of an intracochlear trajectory of said electrodes based on said electrical field spread curves, wherein said intracochlear trajectory comprises a plurality of data points each representing a particular electrode included in said plurality of electrodes and plotted within a graph defined by horizontal and vertical axes representative of electrical distance, and wherein a position of said data points within said graph graphically identifies a location of each of said plurality of electrodes in relation to one another within a cochlea of said patient; and
    providing said graphical representation of said intracochlear trajectory for display by an interface device.

2. The method of claim 1, wherein said electrical field spread curves are represented by an impedance matrix.

3. The method of claim 2, further comprising:
    deriving a distance matrix from said impedance matrix, said distance matrix configured to represent a relative electrical distance between each of said electrodes; and
    performing one or more operations on said distance matrix to generate said graphical representation of said intracochlear trajectory.

4. The method of claim 3, wherein said one or more operations comprises multidimensional scaling.

5. The method of claim 1, further comprising detecting a malfunction of said electrode array based on said intracochlear trajectory.

6. The method of claim 5, wherein said malfunction comprises an improper positioning of one or more of said electrodes.

7. The method of claim 5, wherein said malfunction comprises an anatomical abnormality.

8. The method of claim 1, wherein said using of said electrical field imaging comprises:
consecutively stimulating each of said electrodes; and
measuring an intracochlear potential at each of said electrodes each time one of said electrodes is stimulated.

9. The method of claim 1, wherein said graphical representation of said intracochlear trajectory is configured to convey graphical information that indicates whether at least one of said plurality of electrodes needs to be repositioned within said cochlear implant patient.

10. A system comprising:
a cochlear prosthesis configured to apply stimulation to at least one of a plurality of electrodes configured to be implanted within a cochlea of a patient; and
an interface device selectively and communicatively coupled to said cochlear prosthesis;
wherein said interface device is configured to
direct said cochlear prosthesis to use electrical field imaging to generate an electrical field spread curve for each of said plurality of electrodes;
generate a graphical representation of an intracochlear trajectory of said electrodes based on said electrical field spread curves, wherein said intracochlear trajectory comprises a plurality of data points each representing a particular electrode included in said plurality of electrodes and plotted within a graph defined by horizontal and vertical axes representative of electrical distance, and wherein a position of said data points within said graph graphically identifies a location of each of said plurality of electrodes in relation to one another within said cochlea of said patient; and
display said graphical representation of said intracochlear trajectory.

11. The system of claim 10, wherein said electrical field spread curves are represented by an impedance matrix.

12. The system of claim 11, wherein said interface device is further configured to:
derive a distance matrix from said impedance matrix, said distance matrix configured to represent a relative electrical distance between each of said electrodes; and
perform one or more operations on said distance matrix to generate said graphical representation of said intracochlear trajectory.

13. The system of claim 12, wherein said one or more operations comprises multidimensional scaling.

14. The system of claim 10, wherein said interface device is further configured to facilitate detection of a malfunction of said electrode array based on said intracochlear trajectory.

15. The system of claim 14, wherein said malfunction comprises an improper positioning of one or more of said electrodes.

16. The system of claim 14, wherein said malfunction comprises an anatomical abnormality.

17. The system of claim 10, wherein said cochlear prosthesis is configured to generate said electrical field spread curves by:
consecutively stimulating each of said electrodes; and
measuring an intracochlear potential at each of said electrodes each time one of said electrodes is stimulated.

18. The system of claim 10, wherein said graphical representation of said intracochlear trajectory is configured to convey graphical information that indicates whether at least one of said plurality of electrodes needs to be repositioned within said cochlea of said patient.

19. A system comprising:
an implantable cochlear stimulator configured to apply stimulation to at least one of a plurality of electrodes configured to be implanted within a cochlea of a patient;
a sound processor selectively and communicatively coupled to said implantable cochlear stimulator, said sound processor configured to generate one or more stimulation parameters governing said stimulation; and
an interface device selectively and communicatively coupled to said sound processor;
wherein said interface device is configured to
generate a graphical representation of an intracochlear trajectory of said electrodes in accordance with one or more electrical field spread curves generated by said implantable cochlear stimulator, wherein said intracochlear trajectory comprises a plurality of data points each representing a particular electrode included in said plurality of electrodes and plotted within a graph defined by horizontal and vertical axes representative of electrical distance, and wherein a position of said data points within said graph graphically identifies a location of each of said plurality of electrodes in relation to one another within said cochlea of said patient; and
display said graphical representation of said intracochlear trajectory.

20. The system of claim 19, wherein said interface device is configured to generate said graphical representation of said intracochlear trajectory by:
directing said sound processor to direct said implantable cochlear stimulator to generate an electrical field spread curve for each of said plurality of electrodes; and
using said electrical field spread curves to generate said graphical representation of said intracochlear trajectory.

* * * * *